United States Patent [19]

Dodge

[11] Patent Number: 5,515,558
[45] Date of Patent: May 14, 1996

[54] PORTABLE SHOWER BAG WITH REPLACEABLE HEAT SOURCE

[76] Inventor: James J. Dodge, 375 "A" Owosso Dr., Eugene, Oreg. 97404

[21] Appl. No.: 332,127

[22] Filed: Oct. 31, 1994

[51] Int. Cl.$^6$ ................................................. H47K 3/22
[52] U.S. Cl. ...................................... 4/617; 383/40
[58] Field of Search .................... 4/602, 603, 615, 4/616, 617; 383/38, 901, 40; 604/113

[56] References Cited

U.S. PATENT DOCUMENTS

| | | | |
|---|---|---|---|
| 526,501 | 9/1894 | Plummer | 383/901 X |
| 647,294 | 4/1900 | Cropley | 383/901 X |
| 2,116,009 | 5/1938 | Brown | 383/38 X |
| 2,770,275 | 11/1956 | Suciu | 383/38 X |
| 3,140,716 | 7/1964 | Harrison et al. | 604/113 X |
| 4,188,989 | 2/1980 | Anderson | 383/40 X |
| 4,520,793 | 6/1985 | Hall | 4/616 X |
| 4,819,793 | 4/1989 | Willard et al. | 383/38 X |
| 5,263,929 | 11/1993 | Falcone et al. | 604/89 |
| 5,295,964 | 3/1994 | Gauthier | 604/113 |

*Primary Examiner*—Robert M. Fetsuga
*Attorney, Agent, or Firm*—James D. Givnan, Jr.

[57] ABSTRACT

A water bag is provided with an expanse of material extending across a lower portion of a bag wall to provide a pocket into which may be inserted a heat pack or a heat sink. Conduits are provided on the interior surface of the bag wall adjacent the pocket with bag contents flowing through the conduits and heated by the heat pack in place on the bag exterior. A bag outlet defines a mixing chamber which receives bag contents from multiple passageways. A valve regulates discharge flow from the bag.

9 Claims, 1 Drawing Sheet

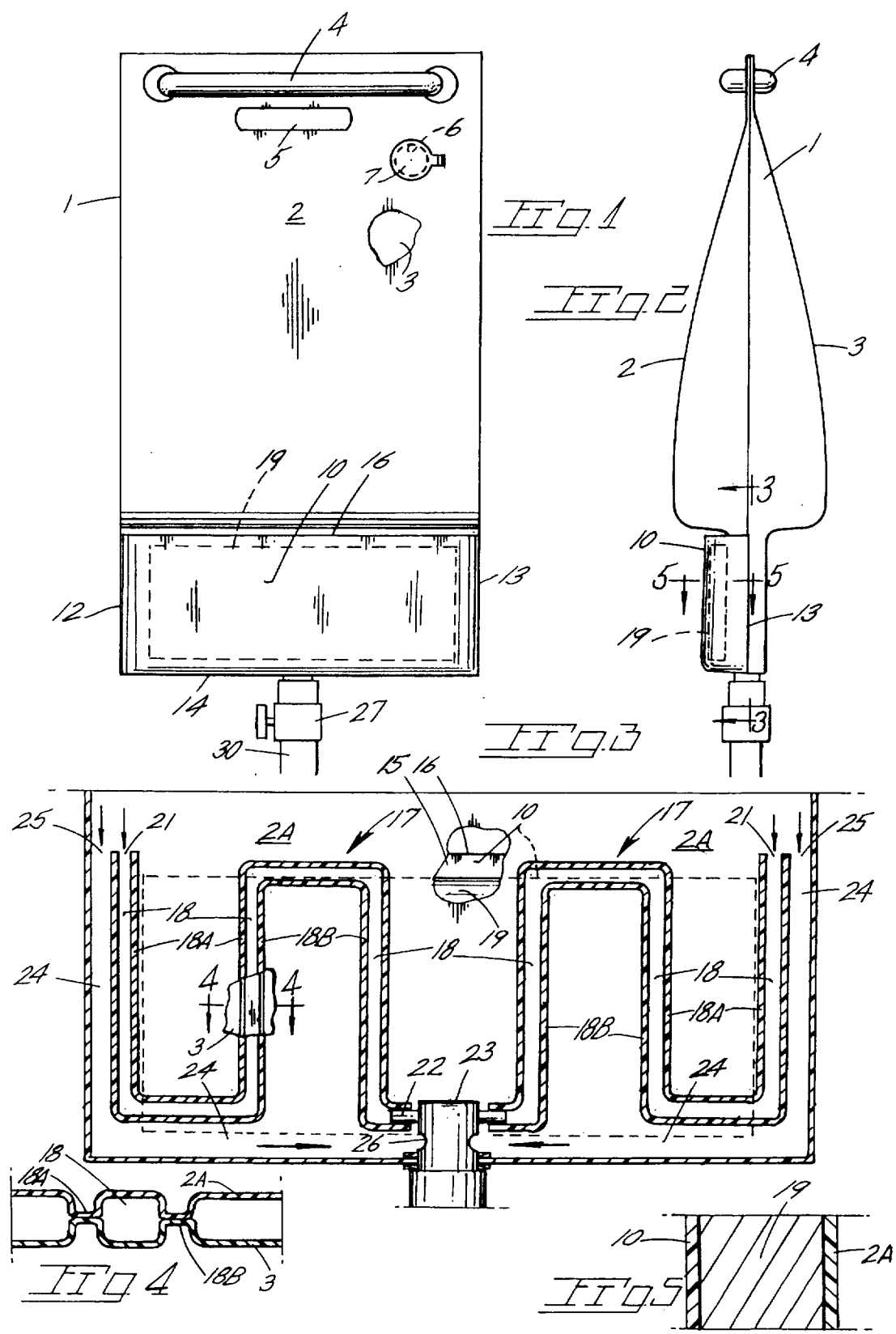

PORTABLE SHOWER BAG WITH REPLACEABLE HEAT SOURCE

BACKGROUND OF THE INVENTION

The present invention pertains generally to portable water containers heated by sources other than electricity.

Available to outdoorsmen are portable, solar heated water bags. An obvious drawback to such bags is the dependency on direct sunlight for a substantial period of time each day. Additionally, the recovery time for the solar heated water bag is considerable. Such portable sources of heated water must be of a manageable size for elevated positioning of same in a convenient manner to permit a gravity flow from the bag. An additional drawback to such bags is the heat loss when such bags are used in low ambient temperature environments.

In the prior art U.S. Pat. No. 5,263,929 discloses a bladder suspended within a bag with the bladder in controlled communication with two chemical agent containers. The agents, upon actuation of the device, enter plural reaction chambers in the bladder whereat heat is conducted to the bag contents. The bladder does not appear to be removably attached to the outer bag.

SUMMARY OF THE PRESENT INVENTION

The present invention pertains generally to a portable water bag having a replaceable heat source such as a chemical pack.

The present water bag includes provision for the removable installation of a heat pack of the type providing an exothermic reaction. Such packs are manufactured by several sources for various uses and are all self-contained and constitute a source of heat when actuated by the user. A holder of the bag serves to retain the heat pack and permits convenient recharging of the pack. The pack, when operatively positioned, is in surface engagement with a bag wall along which water is directed to a bag outlet. Conduit means are formed in the lower portion of the bag and through which bag contents flow in an irregular manner to promote heat transfer. The heat pack is confined by the holder in surface engagement with the bag lower portion.

Important objectives include the provision of a water bag for heating in an efficient manner by a replaceable heat source such as a heat pack; the provision of a water bag having novel structure assuring the routing of a water flow past heated surfaces of the bag; the provision of a bag which permits the mixing of a directed, heated water flow with remaining bag contents.

BRIEF DESCRIPTION OF THE DRAWINGS

In the accompanying drawings:

FIG. 1 is a front elevational view of a water bag embodying the present invention;

FIG. 2 is a side elevational view taken from the right side of FIG. 1;

FIG. 3 is a vertical sectional view taken approximately along line 3—3 of FIG. 2;

FIG. 4 is a horizontal sectional view taken along line 4—4 of FIG. 3; and

FIG. 5 is a horizontal sectional view taken along line 5—5 of FIG. 2.

DETAILED DESCRIPTION OF THE PREFERRED EMBODIMENTS

With continuing attention to the drawings wherein applied reference numerals indicate parts similarly hereinafter identified, the reference numeral i indicates a water bag which may be of a pliable, synthetic material, having a fused seam about its perimeter to join wall members 2 and 3. To render the bag conveniently portable, a handle assembly at 4 may be provided with an opening at 5 enabling gripping of the bag upper end. An inlet opening at 6 is normally closed with a plug 7. Opening 6 preferably includes an internally threaded segment for attachment of a hose end fitting to facilitate filling of the bag and which may be utilized to receive the end of a hose or other conduit exposed to solar energy for the purpose of augmenting the later described heat source.

A retainer 10 is embodied within an expanse of flexible material which is fused, at its edges 12, 13 and 14, to bag 1. An opening 15 is thus provided along a free edge 16 of the retainer and is partially defined by bag wall 2. The pocket thus formed accommodates a unitary heat source 19 and preferably a packet of a chemical composition capable of an exothermic reaction upon actuation by the user, for warming of the bag contents. Such unitary, reusable heat sources are manufactured and sold under various trademarks with a particularly suitable heat source being a pack sold under the trademark ZAP PAC, which is of a size and shape to provide the heat required for the heating of a water bag with a capacity of approximately four gallons. When held in place in a snug manner, as shown in FIGS. 1 and 2, the heat source 19 substantially abuts the width of the bag to heat a lower segment 2A of bag wall 2.

A lower portion of the bag is formed to provide conduit means indicated generally at 17. For the efficient transfer of heat from bag wall 2 it has been determined that the conduit means include one or more primary passageways at 18 formed by partial fusing at 18A–18B of the bag walls 2 and 3 during bag manufacture. The conduit means includes inlets 21 and outlets 22, the latter in communication with an outlet chamber 23. Secondary passageways at 24 have inlets at 25 and are in communication with chamber 23 in openings therein at 26. A valve 27 regulates the discharge flow from the bag. Accordingly water is heated during flow through passageways 18 and is mixed with water heated to a lesser extent moving through secondary passageways 24.

While only one pack retainer 10 is disclosed in place on one wall of the bag, it will be understood that a second pack retainer may be disposed on a remaining bag wall to receive a second heat pack. A hose at 30 may be equipped at its unseen end with a shower head.

As shown in FIG. 5, heat source 19, when in place, is urged into snug surface contact with the bag wall to ensure efficient conduction of heat.

While the term heat source is used in the above description of the present invention it will be understood that a three dimensional endothermic article may be substituted for heat source 19 for the cooling of bag contents by reason of serving as a heat sink.

While I have shown but one embodiment of the invention, it will be apparent to those skilled in the art that the invention may be embodied still otherwise without departing from the spirit and scope of the invention.

Having thus described the invention, what is desired to be secured by a Letters Patent is:

I claim:

1. A portable water bag including, a bag having opposite ends and having an inlet and an outlet each adjacent a respective one of said opposite ends, said bag including a wall member and a retainer located proximate the wall member to define a pocket for reception of a heat source, said retainer being an expanse of material fused to said wall member, conduit means on the bag interior through which water flows from said inlet to said outlet, said conduit means partially embodied in said wall member.

2. The portable water bag claimed in claim 1 wherein said conduit means includes primary and secondary passageways.

3. The portable water bag claimed in claim 1 wherein said bag includes a second wall member, said conduit means embodied in fused portions of said wall member and said second wall member.

4. The portable water bag claimed in claim 3 wherein said conduit means includes primary and secondary passageways and a mixing chamber in communication with said passageways.

5. A portable bag for the storage of a liquid, said bag including, a wall member defining a bag having opposite ends, a retainer proximate the wall member to define a pocket, said wall member and retainer being of fusible material, a bag inlet and an outlet each adjacent a respective one of said opposite ends, an insert for said pocket for altering the temperature of the liquid, and said pocket normally having a cross sectional dimension less than a like cross sectional dimension of said insert to cause displacement of said wall member and said retainer upon insertion of said insert into the pocket to ensure biased contact of the insert with said wall member.

6. The bag claimed in claim 5 additionally including conduit means on the bag interior through which liquid flows from said inlet to said outlet.

7. The bag claimed in claim 6, wherein said conduit means are partially embodied in said wall member.

8. The bag claimed in claim 6, wherein said conduit means includes first and second passageways of dissimilar configuration.

9. A bag for liquids comprising, a bag having walls defining passageways for the liquids, and opposite ends, an inlet and an outlet each adjacent a respective one of said opposite ends, said passageways in communication with said inlet and said outlet, an expanse of flexible material having edges fused to at least one of said walls, said expanse of material offset from said one of said walls to insertably receive a heat source and to urge the heat source into abutment with said passageways to impart heat thereto.

* * * * *

UNITED STATES PATENT AND TRADEMARK OFFICE
CERTIFICATE OF CORRECTION

PATENT NO.   : 5,515,558
DATED        : May 14, 1996
INVENTOR(S)  : Dodge

It is certified that error appears in the above-identified patent and that said Letters Patent is hereby corrected as shown below:

On the title page, item [75] Inventor: "James J. Dodge" should read --James L. Dodge--.

Signed and Sealed this

Sixth Day of August, 1996

Attest:

BRUCE LEHMAN

Attesting Officer        Commissioner of Patents and Trademarks